United States Patent [19]

Foye

[11] 4,367,226
[45] Jan. 4, 1983

[54] N-SUGAR COMPOUNDS, COMPOSITIONS AND USES THEREOF

[76] Inventor: William O. Foye, 7 Winchester Dr., Lexington, Mass. 02173

[21] Appl. No.: 212,198

[22] Filed: Dec. 2, 1980

[51] Int. Cl.³ ............... A61K 31/70; C07H 19/00; C07H 17/00; C07H 5/02
[52] U.S. Cl. ............... 424/180; 536/22; 536/23
[58] Field of Search ............ 536/23, 22, 53, 54, 536/18; 424/176, 361, 180

[56] References Cited

U.S. PATENT DOCUMENTS 4,066,750  1/1978  Smith et al. ............ 536/53
4,109,078  8/1978  Vorbruggen et al. ...... 536/23

OTHER PUBLICATIONS

Bannister, B., J. Antibiotics, vol. 25, pp. 377–386, 1972.

Primary Examiner—Blondel Hazel
Attorney, Agent, or Firm—Norman Blumenkopf

[57] ABSTRACT

Novel, water-soluble antimicrobial compounds are provided which contain a sugar moiety linked to a nitrogen atom of substituted thiourea or a thiazole. The compounds have the general formula:

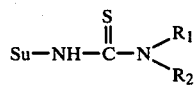

I.

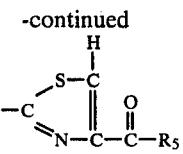

II.

and the pharmaceutically acceptable salts thereof
wherein Su is a sugar moiety, i.e., mono- or polysaccharide and preferably glucosyl or acylated (i.e. $C_2$ to $C_6$ alkanoyl e.g. acetyl, propionyl, butyroyl etc. or aroyl e.g. benzoyl or $C_1$ to $C_4$ alkyl or alkoxy substituted benzoyl) ribosyl; and in Formula I, $R_1$ and $R_2$ are independently hydrogen, $C_1$ to $C_8$ alkyl or alkoxy; $C_1$ to $C_8\omega$-phenyl-(or substituted phenyl)-substituted $C_1$ to $C_8$ alkyl; $C_3$ to $C_8$ alkene, preferably allyl;

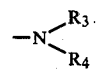

wherein $R_3$ and $R_4$ are independently hydrogen or $C_1$ to $C_8$ alkyl, or the atoms to form a 5- or 6-membered heterocyclic [which may contain $C_1$ to $C_4$ alkyl, $C_1$ to $C_4$ alkoxy, halo (e.g., chloro, bromo or iodo), hydroxy, carboxamido, sulfonamido and the like] such as piperazino, methyl piperazino, pyrimidino, piperidino, morpholino, thiamorpholino, pyrrolyl, pyrrolidinyl, furyl, tetrahydrofuryl and the like, but only one of $R_1$ and $R_2$ is hydrogen, and in Formula II, $R_5$ is oxy($C_1$ to $C_8$)alkyl or substituted alkyl, phenyl or substituted phenyl or $NR_6R_7$ wherein $R_6$ and $R_7$ are independently selected similarly as $R_1$ and $R_2$.

The compounds are particularly useful in aqueous systems especially in cosmetic formulations for maintaining same in a septic state.

Methods for making compounds of Formula I and II are also disclosed.

5 Claims, No Drawings

N-SUGAR COMPOUNDS, COMPOSITIONS AND USES THEREOF

The present invention relates to new water-soluble antimicrobial compounds and in particular to compounds which are of relatively low toxicity, high biological activity and are physically and chemically stable. Such compounds are especially suited for use as preservative agents in cosmetic formulations.

While many rhodanine derivatives have been reported as active against bacteria [J. Pharm. Soc. Japan 74 p. 113 (1954)], fungi [Nature 168 P. 171 (1951); Ind. Eng. Chem. 45 P. 1027 (1953); and Acta Phytopatol. 4 P.345 (1969)] and parasites [J. Parasitol. 53 P.20 (1967); J. Parasitol. 52 P.528 (1966)], and similarly with thioureas (U.S. Pat. No. 4,020,095), they have not generally been found acceptable or have they been used in cosmetics as preservatives because of their toxicities [Gig. Sanit. 10 P.54 (1976); Acta Polon. Pharm. 15 P.471 (1958); and Nature 183 P. 607 (1959)], and because of changes in color, viscosity, and pH in aqueous solution.

It has now been discovered that certain thiourea and thiazole compounds which are linked to a sugar moiety, and particularly a glycosyl or ribosyl group, through a nitrogen atom, exhibit effective anti-microbial activity and have the other desideratums of a preservative particularly for aqueous-based cosmetic compositions.

The compounds of this invention have the general formulae I and II:

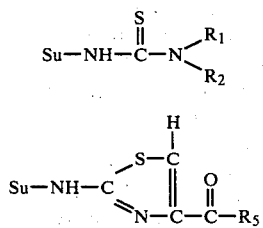

and the pharmaceutically acceptable salts thereof wherein Su is a sugar moiety, i.e., mono- or polysaccharide and preferably glycosyl or acylated (i.e. $C_2$ to $C_6$ alkanoyl e.g., acetyl, propionyl, butyroyl etc. or aroyl e.g. benzoyl or $C_1$ to $C_4$ alkyl or alkoxy substituted benzoyl) ribosyl; and in Formula I, $R_1$ and $R_2$ are independently hydrogen, $C_1$ to $C_8$ alkyl or alkoxy; $C_1$ to $C_8$ ω-phenyl-(or substituted phenyl)-substituted $C_1$ to $C_8$ alkyl; $C_3$ to $C_8$ alkene, preferably allyl;

wherein $R_3$ and $R_4$ are independently hydrogen or $C_1$ to $C_8$ alkyl, or the atoms to form a 5- or 6-membered heterocyclic [which may contain $C_1$ to $C_4$ alkyl, $C_1$ to $C_4$ alkoxy, halo (e.g., chloro, bromo or iodo), hydroxy, carboxamido, sulfonamido and the like] such as piperazino, methyl piperazino, pyrimidino, piperidino, morpholino, thiamorpholino, pyrrolyl, pyrrolidinyl, furyl, tetrahydrofuryl and the like, but only one of $R_1$ and $R_2$ is hydrogen, and in Formula II, $R_5$ is oxy($C_1$ to $C_8$)alkyl or substituted alkyl, phenyl or substituted phenyl or $NR_6R_7$ wherein $R_6$ and $R_7$ are independently selected similarly as $R_1$ and $R_2$.

SUGAR COMPOUNDS

Sugar compounds which may be used in preparing the compounds of this invention include the monosaccharides and oligosaccharides (i.e. di-, tri- and tetra-saccharides). Examples of the monosaccharides are the tetroses, such as threose and erythrose; pentoses such as arabinose, xylose, ribose and lyxose; hexoses, such as glucose, galactose, allose, talose, mannose, fructose and sorbose; heptoses such as glucoheptose, galaheptose and mannoheptose. Octoses, nonoses and decoses may also be used if desired. The sugars may be of the D- or l-form as well as of the α- or β- variety.

PROCESS

The N-sugar N-substituted thiourea compounds of Formula I are readily prepared from the acylated N-sugar rhodanines by aminolysis. This route has many advantages over the possible route via sugar (with protected groups) isothiocyanate and amine. Firstly, the rhodanines are accessible in high yield and secondly the sugar rhodanines have a higher stability than the isothiocyanates. The aminolysis is carried out with the selected amine or amines in a solvent preferably methanol at temperatures varying from about 0° C. to about 100° C. and preferably at about ambient temperatures ranging from about 10° C. to about 50° C. and more preferably at room temperatures of about 15° C. to 30° C. for periods of time varying from a few hours (e.g. 1 to 2) to several or many days (e.g. 2 to 6). The reaction is generally and preferably carried out in a pressure vessel particularly when the reactants and/or solvents are volatile or have significant vapor pressures at the selected reaction temperature.

The amine reactant is employed in amounts varying from an equivalent amount based on the rhodanine compound to 20 times such an amount and preferably from 2 to 20 moles and more preferably from about 5 to about 15 moles per mole of N-sugar rhodanine compound.

The N-sugar aminothiazoles of Formula II are prepared from an N-sugar thiourea and an alkyl (or substituted alkyl) or phenyl (or substituted phenyl) halopyruvate, preferably a bromopyruvate. Generally about equimolar amounts of reactants are used but a slight molar excess of the pyruvate is preferred for maximizing the yields of the thiazole compound. About 10–30% molar excess of pyruvate is thusly preferred. Temperatures of reaction may vary from room temperature to 150° C.

In the aforedescribed processes it is generally preferred to employ an inert solvent such as methanol, ethanol, acetonitrile or the like.

AMINES

The amines useful herein to prepare Formula I compounds are the alkylamines, both mono and diamines of $C_1$ to $C_8$ in each alkyl moiety; the aralkylamines (i.e. aryl-substituted alkyls) e.g. benzylamine, phenylethylamine, alkyl- and alkoxy-substituted phenylalkylamines such as p-methoxybenzylamine, p-ethoxybenzylamine, 4-chlorobenzylamine, 3,4-dimethoxybenzylamine, and the like; heterocyclic amines, preferably 5- or 6-membered rings such as piperazine, N-methylpiperazine, morpholine, thiomorpholine, piperidine, oxazolidines, pyrrolidines and the like; alkenes of $C_3$ to $C_8$ such as allyl and the like.

The following examples will serve to illustrate the present invention without being deemed limitative thereof. Parts are by weight unless otherwise indicated.

EXAMPLE 1

N-β-D-Glucopyranosyl-N',N'-dimethylthiourea

N-(2,3,4,6-Tetra-O-acetyl-β-D-glucopyranosyl)-5-(3,4-dimethoxybenzylidene)rhodanine[32](0.5 g., 0.00082 mole) was added to a solution of 50 ml. of methanol saturated with dimethylamine at 0° in a pressure bottle. The reaction mixture was stirred for 20 hours at room temperature in the pressure bottle with stopper well closed. The mixture was filtered and the filtrate was evaporated to dryness in vacuo below 30°. The residue was recrystallized twice from methanol and acetone, yielding 0.153 g.(70.2%); white powder; m.p. 183°–184°(dec.).

$[\alpha]_D^{25} = -4.40°(C=1.2, DMF)$.

Ir(KBr); 3500–3300(OH or NH), ~2900(CH), 1570(NH), 1440(CH), 1080(C=S), 1020(C—O), 910(β-form) cm$^{-1}$.

$^1$H NMR(Me$_2$SO—d$_6$+D$_2$O); δ5.37(1H$_{1'}$, d, J=8 Hz), 3.60(2H$_{6'}$, m), 3.22(6H, s, 2Me).

Anal. for $C_9H_{18}N_2O_5S \cdot 1/6H_2O$(M.W. 269.32); Calcd.: C, 40.14; H, 6.86; N, 10.40; S, 11.90; Found: C, 40.34; H, 6.76; N, 9.94; S, 11.75.

EXAMPLE 2

N-β-D-Glucopyranosyl-N'-n-butylthiourea

N-(2,3,4,6-Tetra-O-acetyl-β-D-glucopyranosyl)-5-(3,4-dimethoxybenzylidene)rhodanine[32](1 g., 0.0016 mole) was added to a solution of n-butylamine(1.08 g., 0.016 mole) in 50 ml. of methanol in a pressure bottle. The reaction mixture was stirred at room temperature for 20 hours in the pressure bottle with the stopper well closed. The mixture was filtered and the filtrate was evaporated to dryness in vacuo below 30°. The residue was dissolved in the minimum amount of acetone and was set aside at 5° for 18 hours. The white precipitate was filtered, washed with acetone, and dried in vacuo at room temperature, yielding 0.426 g.(80.0%); m.p. 94°–96°(dec.).

$[\alpha]_D^{25} = -15.4°(C=0.54)$.

IR(KBr); 3500–3300(OH or NH), 3100(NH), ~2900(CH), 1550(NH), 1460(CH), 1080(C=S), 1020(C—O), 900(β-form) cm$^{-1}$.

$^1$H NMR(Me$_2$SO-d$_6$+D$_2$O); δ 5.07(1H$_{1'}$, d, J=8 Hz), 3.52(2H$_{6'}$, m), 3.17(2H, m, N—CH$_2$), 1.40(4H, m, N—C—CH$_2$CH$_2$), 0.96(3H, m, Me).

Anal. for $C_{11}H_{22}N_2O_5S \cdot \frac{2}{3}(CH_3)_2CO$(M.W. 333.09); Calcd.: C, 46.87; H, 7.83; N, 8.41; S, 9.63; Found: C, 46.30; H, 7.68; N, 8.42; S, 9.60.

EXAMPLE 3

N-β-D-Glucopyranosyl-N'-p-methoxybenzylthiourea

N-(2,3,4,6-Tetra-O-acetyl-β-D-glucopyranosyl)-5-benzylidenerhodanine(1.102 g., 0.002 mole) was added to a solution of p-methoxybenzylamine(3.5 g., 0.024 mole) in 50 ml. of methanol in a pressure bottle. The reaction mixture was stirred for 19 hours at room temperature in the pressure bottle with the stopper well closed. The mixture was filtered and the filtrate was evaporated to a sticky syrup in vacuo. The residual syrup was dissolved in the minimum amount of acetone, and anhydrous ether was added to the solution to give a sticky yellow solid. The supernatent was decanted, and the residual sticky solid was dissolved in the minimum amount of actone. Ethyl acetate was added to the solution to give a precipitate. The solid was filtered, partially dissolved in ethyl acetate, and then chromatographed on a column of silica gel (1×20 cm) using ethyl acetate as the first solvent, and acetone as the second solvent. Fifty ml. of ethyl acetate effluent was collected in the first Erlenmeyer flask, and 75 ml. of actone effluent was collected in the second Erlenmeyer flask. The volume of the acetone effluent was reduced to ca. 25 ml. and was set aside at 5° for 24 hours. The straw crystals were filtered, washed with ethyl acetate, and dried in vacuo at room temperature, yielding 0.525 g. (73.2%); m.p. 83°–85°(dec.).

$[\alpha]_D^{25} = -20.3°(C=1.1)$.

IR(KBr); 3540(OH), 3500–3300(OH or NH), 3030(aromatic CH), ~2900(CH), 1610(benzene ring), 1550(NH), 1450(CH), 1080(C=S), 1030(C—O), 900(β-form) cm$^{-1}$.

$^1$H NMR(Me$_2$SO-d$_6$+D$_2$O); δ 7.07(4H, m, benzene), 5.07(1H$_{1'}$, bd, J=8 Hz), 3.75(3H, s, OMe), 3.58(2H$_{6'}$, m), 3.20(2H, bs, N—CH$_2$).

Anal. for $C_{15}H_{22}N_2O_6S$(M.W. 358.41); Calcd.: C, 50.27; H, 6.19; N, 7.82; S, 8.96; Found: C, 50.35; H, 6.14; N, 7.69; S, 9.13.

EXAMPLE 4

N-β-D-Glucopyranosyl-N'-β-phenethylthiourea

N-(2,3,4,6-Tetra-O-acetyl-β-D-glucopyranosyl)-5-benzylidenerhodanine (3.31 g., 0.006 mole) was added to a solution of β-phenethylamine (8.72 g., 0.072 mole) in 50 ml. of methanol in a pressure bottle. The reaction mixture was stirred at room temperature for 24 hours in the pressure bottle with the stopper well closed. The mixture was filtered, and the filtrate was evaporated to a sticky syrup below 30° in vacuo. The residue was dissolved in the minimum amount of acetone and was set aside at 5° for 24 hours. The white precipitate was filtered, washed with acetone, and recrystallized from methanol and acetone. It was dried at room temperature in vacuo, yielding 1.61 g. (78.5%); m.p. 87°–89°(dec.).

$[\alpha]_D^{25} = -19.0°(C=1.1)$.

IR(KBr); 3500–3300(OH or NH), 3100(NH), 3030(aromatic CH), ~2900(CH), 1590(benzene ring), 1550(NH), 1070(C=S) 1020(C—O), 900(β-form) cm$^{-1}$.

$^1$H NMR(Me$_2$SO-d$_6$+D$_2$O); δ 7.27 (5H, s, benzene), 5.10(1H$_{1'}$, bd, J=8 Hz), 3.62 (2H$_{6'}$, m), 3.28(2H, bs, N—CH$_2$), 2.90(2H, bd, N—C—CH$_2$).

Anal. for $C_{15}H_{22}N_2O_5S$(M.W. 342.41); Calcd.: C, 52.62; H, 6.48; N, 8.18; S, 9.36; Found: C, 52.35; H, 6.42; N, 7.90; S, 9.61.

EXAMPLE 5

N-β-D-Glucopyranosyl-N'-benzylthiourea

N-(2,3,4,6-Tetra-O-acetyl-β-D-glucopyranosyl)-5-benzylidenerhodanine (2.204 g., 0.004 mole) was added to a solution of benzylamine (2.58 g., 0.024 mole) in 50 ml. of methanol in a pressure bottle. The reaction mixture was stirred at room temperature for 23 hours in the pressure bottle with the stopper well closed. The mixture was filtered, and the filtrate was evaporated to a sticky syrup below 30° in vacuo. The residual syrup was dissolved in the minimum ammount of acetone, and anhydrous ether was added to the solution to give a yellow sticky solid. The supernatant was decanted, and the residual sticky solid was dissolved in the minimum amount of acetone. Benzene was added to the solution to give a precipitate. The precipitate was filtered, partially dissolved in ethyl acetate, and then chromatographed on a column of silica gel (1×20 cm) using ethyl acetate as the first solvent and acetone as the second solvent. Fifty ml. of ethyl acetate effluent was collected in the first Erlenmeyer flask and 75 ml. of acetone effluent was collected in the second Erlenmeyer flask. The volume of the acetone effluent was reduced ca. 25 ml. and was set aside at 5° for 16 hours. The white precipitate was filtered, washed with acetone, and dried at room temperature in vacuo, yielding 0.99 g. (64.2%); m.p. 97°–100°(dec.).

$[\alpha]_D^{25} = -19.1°(C=1.0)$.

IR(KBr); 3500–3300(OH or NH), 3080(NH), 3030(aromatic CH), ~2900(CH), 1630(benzene ring), 1550(NH), 1455(CH), 1080(C=S), 1030(C—O), 900($\beta$-form) cm$^{-1}$.

$^1$H NMR(Me$_2$SO-d$_6$+D$_2$O); δ 7.27(5H, s, benzene), 5.12(1H$_{1'}$, bd, J=8 Hz), 3.58(2H$_{6'}$, m), 3.19(2H, bs, N—CH$_2$).

Anal. for C$_{14}$H$_{20}$N$_2$O$_5$S.(CH$_3$)$_2$CO(M.W. 386.47); Calcd.: C, 52.83; H, 6.78; N, 7.28; S, 8.30; Found: C, 52.69; H, 6.56; N, 7.21; S, 8.10.

EXAMPLE 6

N-$\beta$-D-Glucopyranosyl-N',N'-diethylthiourea

N-(2,3,4,6-Tetra-O-acetyl-$\beta$-D-glucopyranosyl)-5-benzylidenerhodanine (1.102 g., 0.002 mole) was added to a solution of diethylamine (1.76 g., 0.024 mole) in 50 ml. of methanol in a pressure bottle. The reaction mixture was stirred at room temperature for 21 hours in the pressure bottle with the stopper well closed. The mixture was filtered and the filtrate was evaporated to a brownish syrupy material below 30° in vacuo. The residue was dissolved in the minimum amount of acetone, and anhydrous ether was added to the solution to give a sticky solid. The supernatant was decanted, and the residual solid was dried at room temperature in vacuo. The solid was partially dissolved in ethyl acetate to give a slurry, and chromatographed on a column of silica gel (1×20 cm) using ethyl acetate as the first solvent (60 ml.) and acetone as the second solvent (100 ml.). The 100 ml. of acetone effluent was reduced to ca. 25 ml. and was set aside at room temperature. The beige crystals were filtered, washed with acetone, and dried at room temperature in vacuo, yielding 0.51 g. (81.5%); m.p. 106°–109°(dec.)

$[\alpha]_D^{25} = -11.0°(C=1.1)$.

IR(KBr); 3520(OH), 3500–3300(OH or NH), 3100(NH), ~2900(CH), 1550(NH), 1425(CH), 1080(C=S), 1035(C—O), 890($\beta$-form) cm$^{-1}$.

$^1$H NMR(Me$_2$SO-d$_6$+D$_2$O); δ5.40(1H$_{1'}$, d, J=9 Hz), 3.50(2H$_{6'}$, m), 3.21(4H, m, N(CH$_2$)$_2$), 1.17(6H, t, 2Me).

Anal. for C$_{11}$H$_{22}$N$_2$O$_5$S.H$_2$O(M.W. 312.39); Calcd.: C, 42.29; H, 7.74; N, 8.96; S, 10.26; Found: C, 42.57; H, 7.66; N, 8.87; S, 10.34.

EXAMPLE 7

N-$\beta$-D-Glucopyranosyl-4-methylpiperazine-1-thiocarboxamide

N-(2,3,4,6-Tetra-O-acetyl-$\beta$-D-glucopyranosyl)-5-benzylidenerhodanine(1.102 g., 0.002 mole) was added to a solution of N-methylpiperazine(2.40 g., 0.024 mole) in 50 ml. of methanol in a pressure bottle. The reaction mixture was stirred at room temperature for 18 hours. The mixture was filtered and the filtrate was evaporated to a brownish heavy syrup below 30° in vacuo. The residual syrup was dissolved in the minimum amount of acetone, and anhydrous ether was added to the solution to give a sticky precipitate. The supernatant was decanted, and the residual solid was dissolved in the minimum amount of methanol. Anhydrous ether was added to the solution to give a yellow precipitate. The solid was filtered, partially dissolved in ethyl acetate, and then chromatographed on a column of silica gel(1×20 cm) using ethyl acetate as the first solvent(50 ml.) and methanol as the second solvent(200 ml.). The 200 ml. of methanol effluent was reduced to ca. 20 ml. and was set aside at 5° for 24 hours. The white precipitate was filtered, washed with methanol, and dried at room temperature in vacuo, yielding 0.325 g.(50.6%); m.p. 175°–177°(dec.).

$[\alpha]_D^{25} = -12.2°(C=1.2)$.

IR(KBr); 3500–3300(OH or NH), 3060(NH), ~2900(CH), 1530(NH), 1455(CH), 1080(C=S), 1020(C—O), 900($\beta$-form) cm$^{-1}$.

$^1$H NMR(Me$_2$SO-d$_6$+D$_2$O); δ 5.34(1H$_{1'}$, d, J=8 Hz), 3.55(2H$_{6'}$, m), 3.17(4H, unsym. bd, N(CH$_2$)$_2$), 2.33 (4H, m, (CH$_2$($_2$N), 2.20(3H, s, Me).

Anal. for C$_{12}$H$_{23}$N$_3$O$_5$S(M.W. 321.40); Calcd.: C, 44.84; H, 7.21; N, 13.07; S, 9.98; Found: C, 44.94; H, 7.20; N, 12.97; S, 10.13.

EXAMPLE 8

N-$\beta$-D-Glucopyranosylmorpholine-4-thiocarboxamide

N-(2,3,4,6-Tetra-O-acetyl-$\beta$-D-glucopyranosyl)-5-benzylidenerhodanine(1.102 g., 0.002 mole) was added to a solution of morpholine(2.09 g., 0.024 mole) in 50 ml. of methanol in a pressure bottle. The reaction mixture was stirred at room temperature for 31 hours in the pressure bottle with the stopper well closed. The white precipitate was filtered, triturated with methanol, collected by filtration, and dried at room temperature in vacuo, yielding 0.52 g.(79.5%); m.p. 179°–181°.

$[\alpha]_D^{25} = -8.2°(C=1.0, DMF)$.

IR(KBr); 3500(OH), 3400–3200(OH or NH), 3100(NH), ~2900(CH), 1560(NH), 1435(CH), 1060(C=S), 1030(C—O), 900($\beta$-form) cm$^{-1}$.

$^1$H NMR(Me$_2$SO-d$_6$+D$_2$O); δ 5.40(1H$_{1'}$, d, J=8–9 Hz), 3.65(4H, bd, O(CH$_2$)$_2$), 3.60(2H$_{6'}$, m), 3.20(4H, unsym. d, N(CH$_2$)$_2$).

Anal. for C$_{11}$H$_{20}$N$_2$O$_6$S.H$_2$O(M.W. 326.35); Calcd.: C, 40.48; H, 6.80; N, 8.58; S, 9.82; Found: C, 40.68; H, 6.69; N, 8.58; S, 9.65.

EXAMPLE 9

N-$\beta$-D-Glucopyranosylthiomorpholine-4-thiocarboxamide

N-(2,3,4,6-Tetra-O-acetyl-$\beta$-D-glucopyranosyl)-5-benzylidenerhodanine(2.206 g., 0.004 mole) was added to a solution of thiomorpholine(4.953 g., 0.048 mole) in 50 ml. of methanol in a pressure bottle. The reaction mixture was stirred at room temperature for four days. A large amount of white precipitate was filtered and dried at room temperature in vacuo. The residue was triturated with acetone and 1,4-dioxane for two hours, filtered, washed with acetone, and dried at room temperature in vacuo, yielding 0.527 g.(40.6%); m.p. 148°–151°(dec.).

$[\alpha]_D^{25} = +3.05°(C=0.59, DMF)$.

IR(KBr); 3500–3300(OH or NH), ~2900(CH), 1550(NH), 1420(CH), 1070(C=S), 1020(C—O), 890($\beta$-form) cm$^{-1}$.

$^1$H NMR(Me$_2$SO-d$_6$+D$_2$O); δ 5.40(1H$_{1'}$, d, J=8 Hz), 4.10(4H, bd, S(CH$_2$)$_2$), 3.58(2H$_{6'}$, m), 3.20(4H, unsym. d, N(CH$_2$)$_2$).

Anal. for C$_{11}$H$_{20}$N$_2$O$_5$S$_2$(M.W. 324.42); Calcd.: C, 40.72; H, 6.21; N, 8.63; S, 19.77; Found: C, 40.54; H, 6.38; N, 8.31; S, 19.44.

EXAMPLE 10

N-β-D-Glucopyranosyl-N'-allylthiourea

N-(2,3,4,6-Tetra-O-acetyl-β-D-glucopyranosyl)-5-benzylidenerhodanine(2.204 g., 0.004 mole) was added to a solution of allylamine(2.74 g., 0.048 mole) in 50 ml. of methanol in a pressure bottle. The reaction mixture was stirred at room temperature for 24 hours in the pressure bottle with the stopper well closed. The reaction mixture was filtered and the filtrate was evaporated to a syrupy material. The residual syrup was dissolved in the minimum amount of acetone, and anhydrous ether was added to the solution to give a sticky solid. The supernatant was decanted and the residue was dissolved in the minimum amount of acetone. Benzene was added to the solution to give a precipitate. The white precipitate was filtered, partially dissolved in ethyl acetate, and then chromatographed on a column of silica gel(1×20 cm) using ethyl acetate as the first solvent(60 ml.), acetone-ethyl acetate(3:7) as the second solvent(50 ml.), and acetone as the third solvent(80 ml.). The third acetone effluent was reduced to ca.25 ml. and was set aside at 5° overnight. No precipitate was formed. The solution was evaporated to dryness below 30° in vacuo. The formed solid was recrystallized from acetone to give a white precipitate. The precipitate was filtered, washed with acetone, and dried at room temperature in vacuo, yielding 0.591 g. (43.9%); m.p. 95°–97°(dec.).

$[α]_D^{25} = -25.8°(C=1.0)$.

IR(KBr); 3500-3200(OH or NH), 3080(NH), ~2900(CH), 3020(=CH), 1640(C=C), 1550(NH), 1425(CH), 1075(C=S), 1025(C—O), 900(β-form) cm$^{-1}$.

$^1$H NMR(Me$_2$SO-d$_6$+D$_2$O); δ 5.80(1H, m, CH=), 5.21(1H$_{1'}$, d, J=8 Hz), 5.17(2H, m, =CH$_2$), 3.50(2H$_{6'}$, m), 3.17(2H, m, N—CH$_2$), 1.15(1H, s, NH allylamine side).

Anal. for C$_{10}$H$_{18}$N$_2$O$_5$S.(CH$_3$)$_2$CO(M.W. 336.41); Calcd.: C, 46.41; H, 7.19; N, 8.33; S, 9.53; Found: C, 45.95; H, 7.09; N, 8.18; S, 9.36.

EXAMPLE 11

N-β-D-Glucopyranosylpiperidine-1-thiocarboxamide

N-(2,3,4,6-Tetra-O-acetyl-β-D-glucopyranosyl)-5-benzylidenerhodanine(5.52 g., 0.01 mole) was added to a solution of piperidine (6.81 g., 0.08 mole) in 70 ml. of methanol in a pressure bottle. The reaction mixture was stirred at room temperature for 19 hours in the pressure bottle with the stopper well closed. The mixture was filtered and passed through the Dowex-50WX8(cation exchange resin) column(2.54×12 cm) using methanol as eluting solvent. The effluent(120 ml.) was collected, dried with anhydros sodium sulfate, and evaporated to dryness in vacuo. The residue was dissolved in the minimum amount of methanolacetone(2:1) mixture, and then ether was added to give a precipitate. The precipitate was filtered and dried at room temperature in vacuo, yielding 2.21 g.(68.0%); white powder; m.p. 94°–96°(dec.).

$[α]_D^{25} = -15.4°(C=1.1, DMF)$.

IR(KBr); 3500-3300(OH or NH), ~2900(CH), 1550(NH), 1430(CH), 1080(C=S), 1020(C—O), 880(β-form) cm$^{-1}$.

$^1$H NMR(Me$_2$SO-d$_6$+D$_2$O); δ 5.40(1H$_{1'}$, d, J=8 Hz), 3.58(2H$_{6'}$, m), 3.20(4H, m, N(CH$_2$)$_2$), 1.45(6H, bs, 3CH$_2$).

Anal. for C$_{12}$H$_{22}$N$_2$O$_5$S.H$_2$O(M.W. 324.38); Calcd.: C, 44.43; H, 7.46; N, 8.64; S, 9.88; Found: C, 44.17; H, 7.11; N, 8.53; S, 10.10.

EXAMPLE 12

N-β-D-Glucopyranosyl-N'-4-chlorobenzylthiourea

N-(2,3,4,6-Tetra-O-acetyl-β-D-glucopyranosyl)-5-benzylidenerhodanine(5.52 g., 0.01 mole) was added to a solution of 4-chlorobenzylamine(11.33 g., 0.08 mole) in 70 ml. of methanol in a pressure bottle. The reaction mixture was magnetically stirred at room temperature for 24 hours with the stopper well closed. The clear reaction solution was passed through the Dowex-50WX8 (cation exchange resin)column (2.54×18 cm) with additional methanol. The methanol effluent(250 ml.) was collected, filtered, and evaporated to dryness in vacuo. The residue was dissolved in the minimum amount of acetone-methanol(2:1) mixture and stored at −20° for one night. The beige precipitate was filtered and dried at room temperature in vacuo, yielding 2.24 g. (61.7%); m.p. 83°–84°(dec.).

$[α]_D^{25} = +6.2°(C=1.0, DMF)$.

IR(KBr); 3550-3300(OH or NH), 3040(aromatic CH), ~2900(CH), 1600(benzene ring), 1550(NH), 1490(CH), 1080(C=S), 1045(C—O), 880(β-form) cm$^{-1}$.

$^1$H NMR(Me$_2$SO-d$_6$+D$_2$O); δ 7.30(4H, s, benzene), 5.10(1H$_{1'}$, bd, J=9 Hz), 3.60(2H$_{6'}$, m), 3.22(2H, bs, N—CH$_2$).

Anal. for C$_{14}$H$_{19}$N$_2$O$_5$ClS(M.W. 362.83); Calcd.: C, 46.35; H, 5.28; N, 7.72; Cl, 9.77; S, 8.84; Found: C, 46.31; H, 5.40; N, 7.77; Cl, 9.63; S, 8.88.

EXAMPLE 13

N-β-D-Glucopyranosyl-N'-3,4-dimethoxybenzylthiourea

N-(2,3,4,6-Tetra-O-acetyl-β-D-glucopyranosyl)-5-benzylidenerhodanine(5.52 g., 0.01 mole) was added to a solution of 3,4-dimethoxybenzylamine(13.38 g., 0.08 mole) in 70 ml. of methanol in a pressure bottle. The reaction mixture was stirred at room temperature for 18 hours with the stopper well closed. The reaction mixture was stirred with 100 ml. of Dowex-50WX8 resin for 1 hour with 100 ml. of additional methanol and filtered. The filtrate was dried with anhydrous sodium sulfate and filtered. The filtrate was evaporated to a sticky material below 30° in vacuo. The sticky material was dissolved in the minimum amount of chloroform, and poured into 250 ml. of n-hexane to give a precipitate. The crude material was recrystallized from chloroform-n-hexane, yielding 3.57 g.(91.9%); yellow powder; m.p. over 105°(dec.).

$[α]_D^{25} = -1.3°(C=1.0, MeOH)$.

IR(KBr); 3500-3300(OH or NH), 3060(aromatic CH), ~2900(CH), 1520(NH), 1080(C=S), 1025(C—O), cm$^{-1}$.

$^1$H NMR(Me$_2$SO-d$_6$+D$_2$O); δ 7.02(3H, m, benzene), 5.20(1H$_{1'}$, bd, J=9 Hz), 4.60(3H, s, OCH$_3$ at 3), 3.68(3H, s, OCH$_3$ at 4), 3.51(2H$_{6'}$, m).

anal. for $C_{16}H_{24}N_2O_7S$(M.W. 388.44); Calcd.: C, 49.47; H, 6.23; N, 7.21; S, 8.25; Found: C, 50.00; H, 5.92; S, 8.35.

EXAMPLE 14

N-β-D-Glucopyranosylthiourea

N-(2,3,4,6-Tetra-O-acetyl-β-D-glucopyranosyl)-5-benzylidenerhodanine(5.52 g., 0.01 mole) was added to a solution of 50 ml. of methanol saturated with ammonia at 0° in a pressure bottle. The mixture was stirred at room temperature for 18 hours with the stopper well closed. The mixture was evaporated to a syrupy material below 30° in vacuo. The residue was dissolved in the minimum amount of methanol and passed through a silica gel column(2.54×15 cm) with aid of additional methanol. One hundred ml. of effluent was collected and concentrated. During the concentration, a precipitate was formed. The white precipitate was filtered and dried at room temperature in vacuo, yielding 2.04 g. (86.8%); m.p. 207°-209°(dec.). (Lit. m.p. 207°-210°[83], m.p. 211°-212°[32], m.p. 205°-207°[86]).

$[\alpha]_D^{25} = -34.85°$ (C=2.0).

IR(KBr); 3500-3300(OH), 3280-3220($NH_2$), 3100(NH), ~2900(CH), 1650(thioamide NH), 1570(thioamide NH), 1080(C=S), 103(C—O), 910(β-form) $cm^{-1}$.

$^1$H NMR($Me_2SO$-$d_6$+$D_2O$); δ 7.93(1H, d, NH, J=8 Hz, decreased in intensity by adding $D_2O$), 7.25(2H, bs, $NH_2$, decreased in intensity by adding $D_2O$), 5.08(1$H_{1'}$, bd), 3.58(2$H_{6'}$, m).

Anal. for $C_7H_{14}N_2O_5S$(M.W. 238.26); Calcd.: C, 35.29; H, 5.92; N, 11.76; S, 13.46; Found: C, 34.92; H, 6.20; N, 11.54; S, 13.38.

EXAMPLE 15

Ethyl 2-(N-β-D-glucopyranosyl)aminothiazole-4-carboxylate hydrobromide

Ethyl bromopyruvate (8.99 g., 0.047 mole) was added to a suspension of N-β-D-glucopyranosylthiourea (10 g., 0.042 mole) in 120 ml. of hot ethanol, and the reaction was completed by heating 30 minutes. During the heating, the mixture became a clear solution. The reaction solution was evaporated to dryness in vacuo. The residue was crystallized from ethanol and acetone, filtered, and dried at room temperature in vacuo, yielding 16.03 g. (91.9%); white powder; m.p. 162°-163°(dec.).

$[\alpha]_D^{25} = -48.4°$ (C=1.1).

IR(KBr); 3500-3300(OH, 3160(NH), 3095(=CH), ~2900(CH), 1725(C=O), 1610(C=C), 1590 (NH), 1390(CH), 1220(C-O), 1040(C—O), 895(β-form) $cm^{-1}$.

$^1$H NMR($Me_2SO$-$d_6$); δ7.62(1$H_5$, s), 6.09(bs, OH, NH), 4.24(2H, q, $CH_2$ of ethyl), 3.51(2$H_{6'}$,m) 1.30(3H, t, $CH_3$ of ethyl).

Anal. for $C_{12}H_{18}N_2O_7S \cdot HBr$(M.W. 415.25); Calcd.: C, 34.71; H, 4.61; N, 6.75; S, 7.72; Found: C, 34.88; H, 4.71; N, 6.72; S, 7.92.

EXAMPLE 16

2-(N-β-D-Glucopyranosyl)aminothiazole-4-carboxamide

Ethyl 2-(N-β-D-glucopyranosyl)aminothiazole-4-carboxylate hydrobromide (4.15 g., 0.01 mole) was added to a solution of methanol (50 ml.) saturated with ammonia at 0° in a pressure bottle. The reaction mixture was magnetically stirred at room temperature for 48 hours with the stopper well closed. The mixture was evaporated to dryness in vacuo. The residue was mixed with a small amount of ethyl acetate and chromatographed on a column of silica gel (2.54×20 cm) using acetone as the first solvent (300 ml.) and methanol as the second solvent (300 ml.). The methanol effluent was concentrated to ca. 75 ml., and ethyl acetate (500 ml.) was added to give a precipitate. The creamy yellow precipitate was filtered and dried at room temperature in vacuo, yielding 2.77 g. (76.2%); m.p. over 96° (dec.).

$[\alpha]_D^{25} = -22.2°$ (C=1.4).

IR(KBr); 3500-3300(OH or NH), 3060(=CH), ~2900(CH), 1660 (amide NH), 1560(amine NH), 1020(C—O) $cm^{-1}$.

$^1$H NMR($Me_2SO$-$d_6$); δ8.20(1H, d, NH, J=8 Hz), 7.30(1$H_5$, s), 3.50(2H $_{6'}$, m).

Anal. for $C_{10}H_{15}N_3O_6S \cdot 2H_2O \cdot \frac{1}{2}C_2H_5OH$(M.W. 364.37); Calcd.: C, 36.26; H, 6.09; N, 11.53; S, 8.80; Found: C, 36.41; H, 5.62; N, 11.92; S, 8.94.

EXAMPLE 17

N-(2,3,5-Tri-O-benzoyl-β-D-ribofuranosyl)morpholine-4-thiocarboxamide

To a suspension of N-(2,3,5-tri-O-benzoyl-β-D-ribofuranosyl)-5-benzylidenerhodanine(3.32 g., 0.005 mole) in acetonitrile(40 ml.), water(0.5 ml.) was added. Then morpholine(4.38 g., 0.05 mole) was added in small portions with stirring over 10 min. The solution was stirred at room temperature for 2 days. A small amount of precipitate was formed and filtered. The filtrate(red color) was evaporated to a syrupy material and dried in vacuo. The residue was dissolved in the minimum amount of acetone and chromatographed on a column of silica sel(2.54×20 cm) by using acetone as eluting solvent. The fast moving band was collected(50 ml.), evaporated to dryness(redish bubble foam) at room temperature in vacuo, yielding 2.86 g.(96.7%); m.p. 75°-77°.

$[\alpha]_D^{25} = -19.5°$(C=2.3, $CHCl_3$).

IR(KBr); 3060(aromatic CH), ~2900(CH), 1725(C=O), 1600(benzene ring), 1525(NH), 1270(C—O), 1115(C=S), 1030(C=O) $cm^{-1}$.

$^1$H NMR($Me_2SO$—$d_6$); δ9.10(1H, bs, NH), 7.70(15H, m, 3 benzene), 5.86 (1$H_{1'}$, bs), 3.80(2$H_{5'}$, m), 3.68(4H, m, $CH_2$—O—$CH_2$), 3.54(4H, m, $CH_2$—N—$CH_2$).

Anal. for $C_{31}H_{30}N_2O_8S$(M.W. 590.65); Calcd. : C, 63.04; H, 5.12; N, 4.74; S, 5.43; Found: C, 63,12; H, 5.67; N, 4.89; S, 5.64.

EXAMPLE 18

N-(2,3,5-Tri-O-benzoyl-β-D-ribofuranosyl)-N'-ethoxythiourea

To a solution of N-(2,3,5-tri-O-benzoyl-β-D-ribofuranosyl)-5-benzylidenerhodanine(1.66 g., 0.0025 mole) in acetonitrile(40 ml.), pulverized hydroxylamine hydrochloride(0.7 g., 0.01 mole) was added with stirring; then triethylamine(1.4 ml., 0.01 mole) was added dropwise over 5 min. with stirring. The mixture was stirred for an additional hour. The precipitate was filtered, and the filtrate was treated with ethyl acetate(100 ml.) to give a precipitate which was filtered. The ethyl acetate layer was extracted with 0.1M hydrochloric acid(40 ml.), water(2×50 ml.), and saturated sodium chloride solution(50 ml.), dried over anhydrous sodium sulfate, and evaporated. The residue was chromatographed on a column of alumina(neutral, 2.54×15 cm) by using isopropanol as the first solvent (200 ml.) and methanol as the second solvent(200 ml.). The methanol effdluent was evaporated to 40 ml. by volume to give a creamy yellow precipitate. The precipitate was filtered and dried at room temperature in vacuo, yielding 1.32 g.(93.2%); m.p. over 106°(dec.).

$[\alpha]_D^{25} = -13.2°(C=1.1, CHCl_3)$.

IR(KBr); 3075(aromatic CH), ~2900(CH), 1725(C=O), 1600(benzene ring), 1270(C—O), 1110(C=S), 1050(C—O) cm$^{-1}$.

$^1$H NMR(CDCl$_3$) δ8.4(1H, bs, NH), 7.88–7.30(15H, m, 3 benzene), 5,80(1H$_{1'}$, bs), 4.05(2H, q, CH$_2$), 3.95(2H$_{5'}$, m), 1.14(3H, t, CH$_3$).

Anal. for C$_{29}$H$_{28}$N$_2$O$_8$S(M.W. 564.61); Calcd. : C, 61.69; H, 5.00; N, 4.96; S, 5.68; Found: C, 61.88; H, 4.76; N, 4.88; S, 5.62.

In Table 1 there appears a summary of the Rf values, purification solvent systems, melting points and yields of the glucosylthioureas and the glucosylaminothiazoles.

TABLE 1

Rf values, purification solvent systems, melting points, and yields of glucosylthioureas and glucosylaminothiazoles

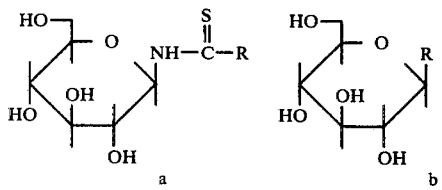

| Type | | R | Rf* | Purification solvent | m.p.(°C.) | Yield(%) |
|---|---|---|---|---|---|---|
| (1) | a | —N(CH$_3$)$_2$ | 0.50 | Acetone/MeOH | 183–184(d) | 70.2 |
| (2) | a | —NH(CH$_2$)$_3$CH$_3$ | 0.72 | Acetone | 94–96(d) | 80.0 |
| (3) | a | —NHCH$_2$—⟨O⟩—OCH$_3$ | 0.65 | (1)E.A. (2)Acetone# | 83–85(d) | 73.2 |
| (4) | a | —NH(CH$_2$)$_2$—⟨O⟩ | 0.75 | Acetone/MeOH | 87–89(d) | 78.5 |
| (5) | a | —NHCH$_2$—⟨O⟩ | 0.76 | (1)E.A. (2)Acetone# | 97–100(d) | 64.2 |
| (6) | a | —N(C$_2$H$_5$)$_2$ | 0.65 | (1)E.A. (2)Acetone# | 106–109(d) | 81.5 |
| (7) | a | —N(piperazinyl-N—CH$_3$) | 0.15 | (1)E.A. (2)MeOH# | 175–177(d) | 50.6 |
| (8) | a | —N(morpholino) | 0.57 | MeOH | 179–181 | 79.5 |
| (9) | a | —N(thiomorpholino) | 0.72 | Dioxane/Acetone | 148–151(d) | 40.6 |
| (10) | a | —NHCH$_2$CH=CH$_2$ | 0.71 | (1)E.A. (2)Acetone# | 95–97(d) | 43.9 |
| (11) | a | —N(piperidino) | 0.66, 0.14** | MeOH/Acetone | 94–96(d) | 68.0 |
| (12) | a | —NHCH$_2$—⟨O⟩—Cl | 0.67 | Acetone/MeOH | 83–84(d) | 61.7 |
| (13) | a | —NHCH$_2$—⟨O⟩(—OCH$_3$)(—OCH$_3$) | 0.54 | (1)E.A. (2)MeOH# | Over 105(d) | 91.9 |
| (14) | a | —NH$_2$ | 0.41, 0.10** | (1)MeOH (2)H$_2$O@ | 207–209(d) | 86.8 |

TABLE 1-continued

Rf values, purification solvent systems, melting points, and yields of glucosylthioureas and glucosylaminothiazoles

| Type | R | Rf* | Purification solvent | m.p.(°C.) | Yield(%) |
|---|---|---|---|---|---|
| (15) b | -NH-⟨S,N⟩-C(=O)-OEt | 0.55 | EtOH/Acetone | 162–163(d) | 91.9 |
| (16) b | -NH-⟨S,N⟩-C(=O)-NH$_2$ | 0.37 | (1)Acetone (2)MeOH# | Over 96(d) | 76.2 |

*Solvent system; Butanol:Acetone:H$_2$O = 4:5:1 (Silica gel)
**With alumina,
Silica gel column,
@Alumina column The corresponding values for the (A) N-(2,3,5-tri-O-benzoyl-β-D-ribofurosyl)morpholine-4-thiocarboxamide (Example 17) and the corresponding (B) N$^1$ ethoxythiourea (Example 18) are as follows:

| Compound | Rf | Purification Solvent | M.P.(°C.) | Yields(%) |
|---|---|---|---|---|
| A | 0.76, 0.69** | Acetone# | 75–77 | 96.7 |
| B | 0.94 | (1) Isopranol@ (2) Methyl alcohol | >106(d) | 93.2 |

**with alumina
silica gel column
@alumina column

The spectroscopic analysis (IR and $^1$H NMR) of the (A) glucosyl thioureas is as follows:

The assignment of the individual infrared peaks of the glucosylthioureas was made by the step by step comparison with the peaks of the reactants. As the products, glucosylthioureas, were formed from tetra-O-acetyl-β-D-glucopyranosylrhodanines, it was observed that the characteristic acetylglucosylrhodanine peaks, 1750(acetyl C=O), 1700–1675(rhodanine C=O), and 1240(C=S) cm$^{-1}$ were disappeared and new peaks were shown at 3500–3300(OH or NH), 1570–1520(NH), 1080–1060(C=S), 1045–1020(C—O), and 920–890(β-glycosidic linkage) cm$^{-1}$.

Characteristic IR peaks of acetylglucosylrhodanines

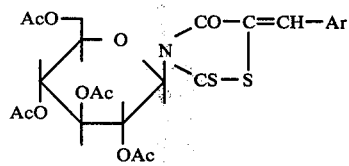

| Frequency(cm$^{-1}$) | Functional group |
|---|---|
| 1750 | Acetyl C=O |
| 1700–1675 | Rhodanine C=O |
| 1240 | Rhodanine C=S |

Characteristic IR peaks of glucosylthioureas

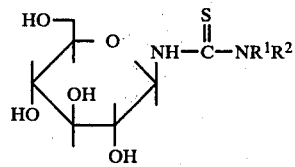

| Frequency(cm$^{-1}$) | Functional group |
|---|---|
| 3500–3300 | OH or NH |
| 1570–1520 | NH |
| 1080–1060 | C=S |
| 1045–1020 | C—O |
| 920–890 | β-linkage |

The appearance of a broad peak at 3500–3300 cm$^{-1}$ represents hydrogen bonded OH groups of sugar, and no peak at the range of 1800–1675 cm$^{-1}$ indicates that the acetyl esters and the rhodanine ring are completely hydrolyzed to form glucosylthioureas without having any protective groups on OH groups. Also, the $^1$H NMR spectrum shows no evidence of retaining the protective acetyl groups by the disappearance of peaks of acetyl groups in the 1.9–2.1 ppm(δ) region.

In the ¹H NMR spectra, the peak for the anomeric proton appeared in the range of 5.07–5.40 ppm(δ) as a doublet. The spin-spin coupling constant(J value) for $H_{1'}-H_{2'}$ was 8–9 Hz which indicated that the glycosidic linkage had a β-configuration($H_{1'-2'}$ trans). The peak appearing at 3.41–3.60 ppm(δ) was assigned to the methylene protons of $C_6$ as it was done in glucose by Lenz and Heeschen[1]. They thought that were electron densities around the proton the only consideration, the methylene protons should have been assigned the lower δ value, as the $C_6$ carbon atom should be comparatively more electron rich than the $C_2$, $C_3$, $C_4$, and $C_5$ ring carbon atoms, each of which was bracketed by two carbinol functions. Also, Fox et al.[2] assigned the lowest δ value to the methylene protons in 5-(β-D-arabinofuranosyl)pyrimidine, a C-nucleoside. The peak for NH(glycosidic) appeared in the 7.25–8.40 ppm(δ) region(broad doublet, J=8 Hz) before treatment with $D_2O$.

(1) J. Poly. Sci. 51; P.247 (1961)
(2) J. Hetero. Chem. 13; P.933 (1976).

Characteristic ¹H NMR peaks of glucosylthioureas

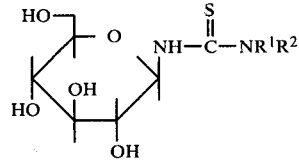

| Chem. shift(ppm; δ) | Assignment |
| --- | --- |
| 3.51–3.60 | $2H_{6'}$, m, methylene H |
| 5.07–5.40 | $1H_{1'}$, d, anomeric H |
| 7.25–8.40 | 1H, bd, NH(glycosidic; J = 8–9 Hz) |

Lenz and Heeschen* made an assignment for the α- and β-configuration of the anomeric proton of glucose along with the value of the coupling constant(J value). They concluded that the α-anomeric proton(1,2cis) had a J value of 2.4 Hz in glucose and the β-anomeric proton(1,2 trans) had a value of 7.5 Hz. This assignment agreed well with the Karplus observation[3] in which the J value, 8–10 Hz, was measured for the axial-axial(1,2 trans) protons of cyclohexane and the J value, 2–3 Hz, was obtained for the axial-equatorial(1,2 cis) protons. Shibata et al.[4] established a β-configuration of the glycosidic linkage of a saponin structure, 6,20-di-0-β-glucosyl-20S-protopanaxatriol, with a J value of 7 Hz.

Supra;
(3) J. Amer. Chem. Soc. 85; P.2870 (1963);
(4) Tetrahedron; 27; P.888 (1971).

Igarashi and Honma[5] assigned the peak at 5.90 ppm(δ) (d, J=4 Hz) in the NMR spectrum of 3,4,6-tri-O-acetyl-2-deoxy-2-thiocyanato-D-glucopyranosylisothiocyanate to an α-anomeric proton(cis configuration), and assigned the peak at 5.83 ppm(δ) (d, J=9 Hz) in the NMR spectrum of 1,3,4,6-tetra-O-acetyl-2-deoxy-2-thiocyanato-D-glucopyranose to a β-anomeric proton(trans configuration).

(5) J. Org. Chem. 32; P. 2521 (1967).

For the glucosyl aminothiazoles the peak at 1725 $cm^{-1}$ in the IR spectrum of the glucosylaminothiazole carboxy ester was due to a C=O stretching vibration of the ethyl carboxylate. The peaks at 1660 $cm^{-1}$, 1610 $cm^{-1}$, 1590–1560 $cm^{-1}$, and 1040–1020 $cm^{-1}$ corresponded to $CONH_2$, C=C (or C=N), NH, and C—O, respectively.

Characteristic IR peaks of glucosylaminothiazoles

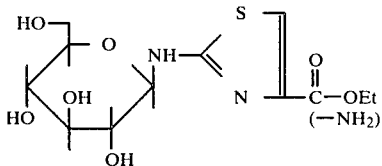

| Frequency($cm^{-1}$) | Functional group |
| --- | --- |
| 3500–3300 | OH or NH |
| 1725 | C=O of ethylcarboxylate |
| 1660 | $CONH_2$ of carboxamide |
| 1610 | C=C or C=N |
| 1590–1560 | NH of amino group |
| 1040–1020 | C—O |

The most characteristic ¹H NMR peak of the glucosylaminothiazoles was the singlet at 7.30–7.62 ppm(δ) region due to a single proton at position 5 of the thiazole ring. The other significant peak was the NH peak (broad doublet, J=8 Hz) at 8.20 ppm(δ)in the ¹H NMR spectrum of 2-(β-D-glucopyranolsyl)aminothiazole-4-carboxamide. In the literature, the thiazole protons showed their chemical shifts[41] at 8.17 ppm(δ)(singlet) in ethyl 2-(2,3,5-tri-O-benzoyl-β-D-ribofuranosyl)thiazole and 8.25 ppm(δ)(singlet) in 2-β-D-ribofuranosylthiazole-4-carboxamide. Takahashi et al. (*) assigned the peak at 8.15–8.28 ppm(δ)(doublet, J=8 Hz) to the amino proton, NH in 8-glucosylaminotheophyllines, which agreed well with our assignment of the NH proton in 2-(β-D-glucopyranosyl)-aminothiazole-4-carboxaamide.

*Chem Pharm. Bull., 27, p. 1153 (1979).

The methylene protons of the sugar moiety appeared at 3.50–3.51 ppm(δ)(multiplet) but for the anomeric proton, no assignment was made because of the unclear peak feature.

Characteristic ¹H NMR peaks of glucosylaminothiazoles

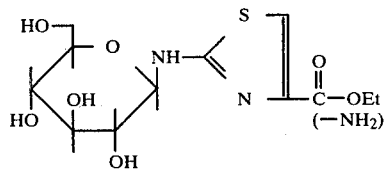

| Chem. shift(ppm; δ) | Assignment |
| --- | --- |
| 3.50–3.51 | $2H_{6'}$, m, methylene H |
| 7.30–7.62 | $1H_5$, s, thiazole H |
| 8.20 | 1H, d, J = 8 Hz, NH |

The features of the IR spectrum of the ribosyl thioureas were similar to the glucosyl thioureas.

In testing for the anti-microbial activity five different types of organics were selected: *Staphyloccoccus aureus, Escherichia coli, Pseudomonas aeruginosa, Candida albicans,* and *Aspergillus niger.* The inclusion of *Asperigillus niger* and *Pseudomonas aeruginosa* in the inocula is recommended to ensure a wide range of protection because these ubiquitous organisms grow in a large variety of formulations and relatively resistant to antimicrobial agents. The incidence of contaminated cosmetics has been the subject of several investigations [6][7]. Pseudomonas was the predominant organism found.

[6] CTFA Cosmet. J. 1; P. 34 (1969);
[7] Am. Cosmet. Perf. 87; P. 63 (1972).

Microbial spoilage of cosmetic preparations was the major concern of manufacturers in former years [8]. Spoilage in this context is defined as microbial growth that results in various deleterious effects such as noxious odors and gases, changes in pH, viscosity, and color, and the destruction of emulsions. The presence of a visible mass of growth or bacterial slime on the surface of a product obviously renders it unsuitable for marketing.

[8] Monowitz, Developments in Industrial Microbiology II, Plenum Press, N.Y. 1961.

Test organism

One Gram-positive, two Gram-negative bacteria, one each of a yeast and a mold were selected for the test. These were, respectively, *Staphylococcus aureus*-(A.T.C.C. 6538), *Escherichia coli*(A.T.C.C. 11229), *Pseudomonas aeruginosa*(A.T.C.C. 15442), *Candida albicans*(A.T.C.C. 10259), and *Aspergillus niger*(A.T.C.C. 1015).

Preparation of inoculum

Portions of four or five discrete colonies representative of the organisms to be tested were inoculated into 10.0 ml. of a suitable broth medium and marked accordingly. The inoculated tubes were incubated at 37° for *S. aureus, E. coli,* and *P. aeruginosa,* and at 25° for *C. albicans* and *A. niger* for 18–24 hours.

Agar plate streak method for qualitative evaluation

Medium: Trypticase Soy Agar(BBL) was used for bacteria, and Sabouraud Maltose Agar(BBL) for the yeast and the mold.

Inoculation of agar plates and incubation: A 10 cm. round plastic plate was used for the preparation of medium. Each plate was divided into four areas by marking on the bottom of the plate. The agar plate was streaked by the appropriate inoculation loop. Three thin loopful of inocula were applied for covering the complete agar plate. Approximately 10–15 mg. of compound to be tested was placed at the corresponding area of each inoculated plate. The plates inoculated with *S. aureus, E. coli,* and *P. aeruginosa* were incubated at 37° for 24–48 hours, and those incubated with *C. albicans* and *A. niger* were incubated at 25° for 48–72 hours.

Interpretation and result: After incubation, if a zone of inhibition was visible around the compound placed, the susceptibility of the organism to the compound was considered to be positive. The degree of positiveness of the compound was decided by the size of the zone.

Broth dilution method for the determination of the Minimal Inhibitory Concentration(MIC)

Quantitative evaluation was made for the compounds which showed some inhibitory activities in the primary agar plate screening test against any of the five organisms. The broth dilution method was chosen for the determination of the MIC. A $10^{-1}$ molar stock solution was prepared by dissolving or suspending the required amount of compound in the sterilized distilled water. The desired number of sterile test tubes were aseptically filled with 9.0 ml. of Trypticase Soy Broth(BBL). 1.0 ml. of the stock solution was added to the first tube and mixed thoroughly. With a sterile pipette, 1.0 ml. was transferred from the first tube to the second tube. After thorough mixing of the contents of the second tube, 1.0 ml. was transferred with a separate pipette to the third tube. This process was continued through the next-to-last tube, from which 1.0 ml. was removed and discarded. Eventually, a serial dilution of $10^{-2}$, $10^{-3}$, $10^{-4}$, $10^{-5}$, and $10^{-6}$ molar concentrations was made. The sixth tube without any antimicrobial agent served as a growth control and also a blank tube was prepared, separately. Except the blank tube, the inoculum was prepared by adding 0.05 ml. of 24 hour-old broth culture without any dilution. The tubes were incubated for 24–48 hours at 37° for bacteria and for 48–72 hours at 25° for the yeast and the mold.

The lowest concentration of antimicrobic resulting in complete inhibition of visible growth represented the MIC; a very faint haziness or a small clump of possible growth was disregarded, whereas a large cluster of growth or definite turbidity was considered evidence that the compound had failed to inhibit growth completely at that concentration.

Of particularly outstanding activity was N-$\beta$-D-glucopyranosyl-N'-allylthiourea against *S. Aureus*($10^{-4}$ M.I.C.), N-$\beta$-D-glucopyranosyl-N'-butylthiourea against *C. Albicans* and *A. Niger,* N-$\beta$-D-glucopyranosyl-N'-benzylthiourea against *E. Coli* and *P. Aeruginosa* as did N-$\beta$-D-glucopyranosyl piperidine-1-thiocarboxamide against *P. Aeruginosa.* N-$\beta$-D-glucopyranosyl-N'-p-chlorobenzylthiourea showed broad inhibitory activities against *S. Aureus, E. coli,* and *C. albicans.* Ethyl 2-(N-$\beta$-D-glucopyranosyl)aminothiazole-4-carboxylate showed broad activities against 4 organisms but not against *A. Niger.*

The toxicity of some of the compounds was ascertained in an $LD_{50}$ test.

The $LD_{50}$ tests were performed for the following compounds; N-$\beta$-D-glucopyranosyl-N'-n-butylthiourea, N-$\beta$-D-glucopyranosyl-N'-benzylthiourea, N-$\beta$-D-glucopyranosyl-piperidine-1-thiocarboxamide, N-$\beta$-D-glucopyranosylthiourea, and ethyl 2-(N-$\beta$-D-glucopyranosyl)aminothiazole-4-carboxylate. The compounds were administered intraperitoneally dissolved or suspended in normal saline by 20–25 gm Charles River CD-1 male mice.

Two animals received 1000 mg/kg and one animal received 2000 mg/kg. With the exception of the animal given by ethyl 2-(N-$\beta$-D-glucopyranosyl)aminothiazole-4-carboxylate at 2000 mg/kg, all animals survived the acute effects and appeared normal after 1 week. Soon after the administration of the compounds, all animals showed decreased activity and labored respiration with the effects more pronounced at the higher dose. All animals recovered within three hours with the above mentioned animal dying two days later.

The following techniques and equipment mentioned herebefore were used.

Thin Layer Chromatography

The thin layer chromatography was performed on Eastman silica gel plates with fluorescent indicator or alumina plates. For the glycosides, the following system was especially efficient: n-Butanol:Acetone:$H_2O$(4:5:1).

Column Chromatography

The column chromatography was carried out with a cylindrical column(2.54×40.0 cm) equipped with a stopcock. Silica gel (100–200 mesh) and alumina (100–200 mesh) were used as packing materials.

Melting Points

All melting points were taken on a Mel-Temp capillary point block and are uncorrected.

Infrared Absorption Spectra

The infrared absorption spectra were recorded on a Perkin-Elmer 457A Grating Infrared Spectrophotometer.

Nuclear Magnetic Resonance Spectra

The nuclear magnetic resonance spectra were determined on a Varian T60 spectrophotometer using tetramethylsilane as an internal standard.

Optical Rotations

The optical rotations were measured by a Perkini-Elmer Polarimeter 241MC and a Carl-Zeiss Polarimeter.

The compositions of this invention are of particular utility in aqueous cosmetic formulations to inhibit bacterial growth. Reference is hereby made to cosmetic formulations as disclosed in the following U.S. Pat. Nos.: (1) 4,159,318 (2) 4,164,564, (3) 4,137,302, (4) 4,148,875, (5) 4,001,141, (6) 4,048,338, (7) 3,919,430 and (8) 3,957,970 as exemplary of formulations with which the present thioureas and thiazoles can be used; thus, Example 4 of U.S. Pat. No. 4,137,302 discloses ethyl p-dimethylaminobenzoate (0.75%). The compound of Example 10 in lieu of the benzoate gives excellent preservative action.

In Example 6 of U.S. Pat. No. 4,048,338, the 0.18 parts of methyl p-hydroxybenzoate is replaced by equal parts of the compound of Example 10 on the one hand and that of Example 12 on the other hand. Again excellent preservative action is obtained.

In Examples I and III of U.S. Pat. No. 3,957,970, the 0.05% preservative is replaced by an equal amount of the compounds of Examples 10, 12 and 15 (separately) and in each instance excellent preservation against bacterial combination is obtained. Each of the foregoing U.S. Patents (1) to (8) is hereby incorporated by reference thereto.

In the cosmetic formulations contemplated herein, the amount of the anti-microbial compound may vary from about 0.0001% to about 5% of the total composition, with the effective amounts, of course, varying depending upon the particular composition.

I claim:

1. A water-soluble compound of the formula:

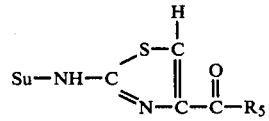

wherein Su represents glucopyranosyl or acylated ribofuranosyl, said acylated moiety being selected from the group consisting of $C_2$ to $C_6$ alkanoyl, benzoyl and $C_1$ to $C_4$ alkyl or alkyoxy benzoyl; and $R_5$ is selected from the group consisting of oxy ($C_1$ to $C_8$) alkyl, and $NR_6R_7$ wherein $R_6$ and $R_7$ are independently selected from the group consisting of hydrogen and $C_1$ to $C_8$ alkyl; and the pharmaceutically acceptable salts thereof.

2. A compound as defined in claim 1 wherein the sugar moiety is glucosyl.

3. A compound as defined in claim 1 wherein the sugar moiety is ribosyl.

4. A thiazole compound as defined in claim 2 wherein $R_5$ is ethoxy.

5. A method for preserving aqueous organo cosmetic compositions comprising incorporating therewith an effective amount of from about 0.001% to about 5%, of a compound of claim 1.

* * * * *